(12) United States Patent
Koo et al.

(10) Patent No.: US 7,881,771 B2
(45) Date of Patent: Feb. 1, 2011

(54) BONE REPOSITION DEVICE, METHOD AND SYSTEM

(75) Inventors: Terry K. K. Koo, Kowloon (HK); Arthur F. T. Mak, Kowloon (HK); Edmund Y. S. Chao, Corona, CA (US)

(73) Assignee: The Hong Kong Polytechnic University, Hong Kong (CN)

( * ) Notice: Subject to any disclaimer, the term of this patent is extended or adjusted under 35 U.S.C. 154(b) by 1582 days.

(21) Appl. No.: 11/195,852

(22) Filed: Aug. 3, 2005

(65) Prior Publication Data
US 2007/0043354 A1 Feb. 22, 2007

(51) Int. Cl.
*A61B 5/05* (2006.01)
*A61B 17/56* (2006.01)
*A61B 17/00* (2006.01)
*A61B 17/58* (2006.01)

(52) U.S. Cl. .............. 600/426; 600/414; 600/424; 606/53; 606/54; 606/102

(58) Field of Classification Search ......... 600/414–415, 600/426, 424; 606/53–54, 57, 102, 86, 105, 606/60
See application file for complete search history.

(56) References Cited

U.S. PATENT DOCUMENTS

| | | | |
|---|---|---|---|
| 4,628,922 A | 12/1986 | Dewar | 128/92 |
| 5,397,322 A | 3/1995 | Campopiano | 606/57 |
| 5,971,984 A | 10/1999 | Taylor et al. | 606/54 |
| 6,328,737 B1 | 12/2001 | Moorcroft et al. | 606/57 |
| 6,837,892 B2 * | 1/2005 | Shoham | 606/130 |
| 2005/0107726 A1 * | 5/2005 | Oyen et al. | 602/16 |

FOREIGN PATENT DOCUMENTS

| | | |
|---|---|---|
| CN | 1571651 | 1/2005 |
| WO | WO 03/030759 | 4/2003 |

OTHER PUBLICATIONS

Ellis et al, 1996, Investigative Radiology 31, pp. 658-667, Use of a Biocompatible Fiducial Marker in Evaluating the Accuracy . . . .
Kim et al, 2002, Jour of Biomechanics 35, pp. 1047-1058, Kinematic Simulation of Fracture Reduction and Bone Deformity . . . .
Koo et al, 2004, 11$^{th}$ World Congress . . . Prosthetics & Orthotics, Determination of Fixator configuration to Facilitate . . . .

(Continued)

*Primary Examiner*—Eric F Winakur
*Assistant Examiner*—Katherine L Fernandez

(57) ABSTRACT

A bone reposition device includes first and second bone supports for supporting first and second portions of a fracture or osteotomize bone about a fracture or osteotomize site, a plurality of sequentially connected connection members and a plurality of joints each with at least a pair of adjacent parts for connecting the connection members therebetween and to the first and second bone supports. The plurality of joints includes at least six joints, each of which possesses one degree of freedom and allows controllable relative rotation or translation of said pair of adjacent parts about one of three axes respectively.

27 Claims, 11 Drawing Sheets

OTHER PUBLICATIONS

Koo et al, 2005, Jour of Biomechanics, pp. 1-9, Development and Validation of a New Approach for Computer-aided Long Bone . . . .

Koo et al, 2005, Jour of Biomechanics, pp. 1-2, Determination of Spatial Relationship Between Fracture Fragments: A . . . .

Koo et al, 2005, 4$^{th}$ Annual Conf . . . Soc Computer Assisted Ortho-Paedic Surgery, pp. 376-377, A New Approach for Computer- . . . .

Tsao et al, 1998, Jour of Computer Assisted Tomography 22, pp. 615-620, Computer-assisted Qualification of Periaxial Bone . . . .

* cited by examiner

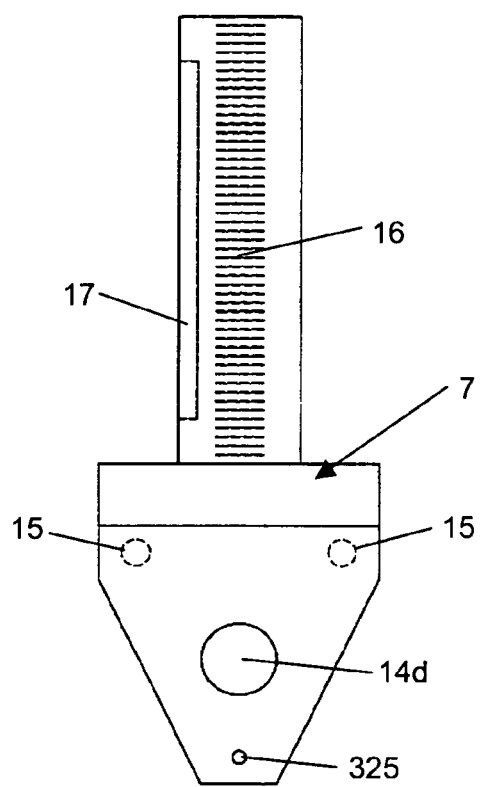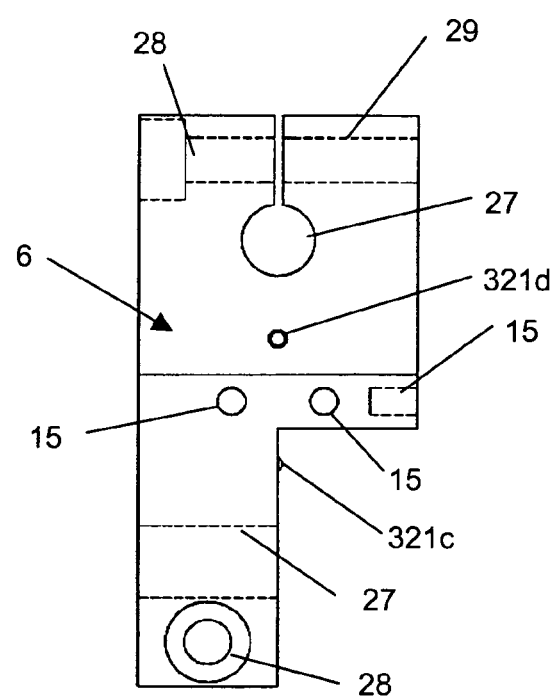
Figure 4
Figure 5

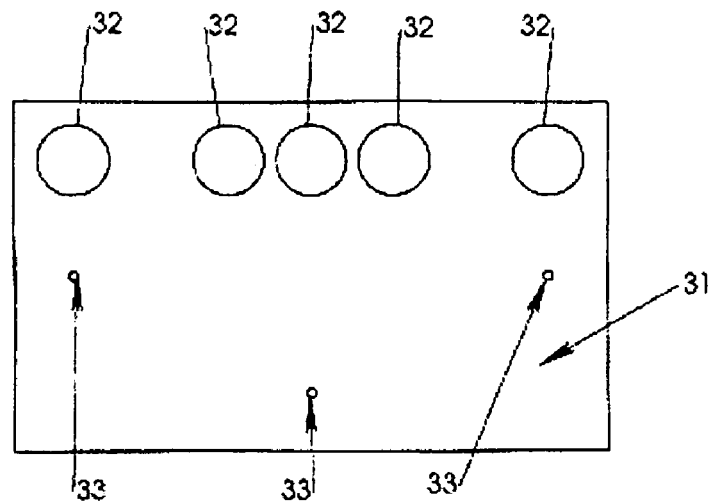
Figure 6
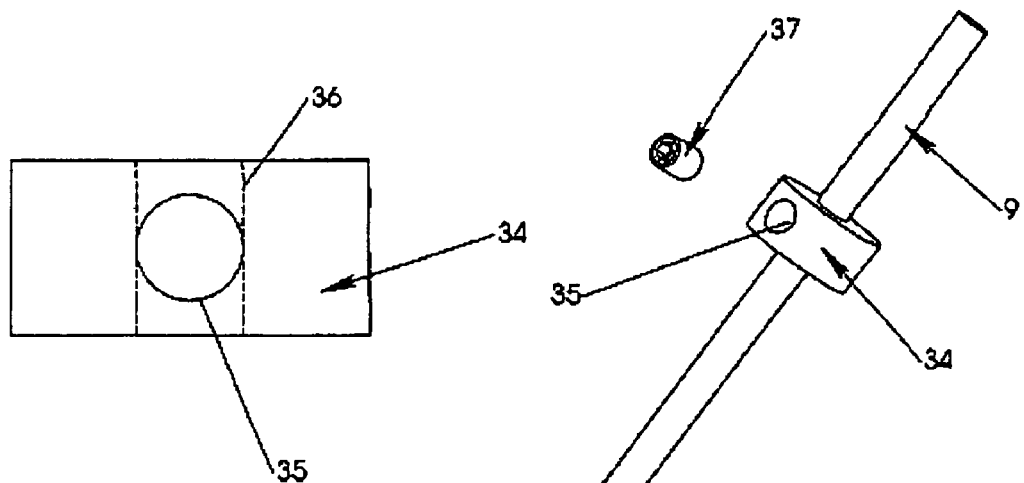
Figure 7
Figure 8

BONE REPOSITION DEVICE, METHOD AND SYSTEM

BACKGROUND

1. Field of the Invention

The present invention relates to a system including an external device and its accessories, for use in orthopaedic surgical applications, and more particularly to a method of using the device to reposition and fix one bone segment relative to another bone segment.

2. Background of the Invention

In various orthopaedic applications, it is often necessary to position and secure two bone segments relative to each other. Operative treatment of long bone fractures is a typical example. A variety of techniques are known for holding together the parts of a fractured bone while healing takes place. One such technique is external fixation, in which pins are inserted into the bone on each side of the fracture point, and which are then connected to a frame by adjustable clamps. The clamps can then be tightened to hold the parts of the bone fixed with respect to each other.

Conventional external fixator designs generally lack enough degrees of freedom to facilitate the bone realignment process. For example, U.S. Pat. No. 4,621,627, entitled "External axial fixation device" and issued to DeBastiani et al. on Nov. 11, 1986, and U.S. Pat. No. 5,788,695, entitled "Patient-operated orthopedic devices" and issued to Richardson on Aug. 4, 1998, disclose external fixator designs using two ball-and-socket joints and one telescopic joint and thus may allow three-dimensional adjustment. However, due to the nature of the ball-and-socket joints, controllable adjustments may be difficult. In addition, U.S. Pat. No. 5,662,650, entitled "Method and apparatus for external fixation of large bones" and issued to Bailey et al. on Sep. 2, 1997, discloses an external fixator design using four revolute joints, one central rotary joint, and two telescopic joints and thus may allow three-dimensional adjustment. However, their serrated locking mechanism of the revolute joints does not allow positioning and fixing of the joints at arbitrary positions. Therefore, controllable adjustments may be difficult. In addition, many of the current joint designs do not facilitate direct readout of the joint position. Therefore, controllable adjustments may be even more difficult.

In current clinical practice, fracture reduction using external fixator can be regarded as a trial and error process. Generally, the surgeon is provided with a two-dimensional image obtained by using X-ray or C-arm, based on which image, the surgeon needs to manipulate the fracture site to realign the proximal and distal fragments. This process involves repeated unlocking the fixation joints, manipulating the fracture site, re-locking the fixation joint, and reviewing the static two-dimensional fluoroscopic images. Given that the fracture deformity is three-dimensional in nature, it can be quite difficult to reduce a three-dimensional deformity based on the limited field-of-view and static two-dimensional images. Significant skills may be required by the surgeon to mentally recreate the spatiotemporal relationship between the fracture fragments and maintain eye-hand coordination while performing the adjustments. Furthermore, when the fixation joints are loosened, stability of the configuration so far achieved could be affected. Therefore, such conventional fracture reduction process may be unnecessarily subjective and time-consuming, and the reduction accuracy can be experience-dependent. This process may sometime cause excessive tissue disruptions around the fracture site, which would compromise the tissue integrity and delay fracture healing. Moreover, this process may predispose the surgeons and patients to excessive amount of radiation.

OBJECT OF THE INVENTION

Therefore, it is an object of the present invention to provide an improved external fixation device, which allows controllable three-dimensional adjustment, or at least provide the public with a useful choice.

It is a further object of the present invention to provide an improved bone realignment process and system, adjustment of which can be more accurate as compared to conventional processes, or at least provide the public with a useful choice.

SUMMARY OF THE INVENTION

According to an aspect of the present invention, a bone reposition device includes first and second bone supports for supporting first and second portions of a fractured or osteotomized bone about a fracture or osteotomize site, a plurality of sequentially connected connection members and a plurality of joints each with at least a pair of adjacent parts for connecting the connection members therebetween and to the first and second bone supports. The plurality of joints includes at least six joints, each of which possesses one degree of freedom and allows controllable relative rotation or translation of said pair of adjacent parts about its respective axis, and the six axes extend at a degree relative to each other.

According to a second aspect of the present invention, a process for reducing fracture of a fractured bone, the fractured bone having first and second portions about a fracture site, includes
  attaching a bone reposition device to the fractured bone, the bone reposition device including
    first and second bone supports for supporting said first and second bone fragments;
    a plurality of sequentially connected connection members; and
    a plurality of joints each with at least a pair of adjacent parts for connecting the connection members therebetween and to the first and second bone supports,
    wherein the plurality of joints includes at least six joints, each of which possesses one degree of freedom and allows controllable relative rotation or translation of said pair of adjacent parts about its respective axis, and wherein the six axes extends at a degree relative to each other,
  scanning the fractured bone for obtaining a three-dimensional image of the fracture fragments;
  determining an adjustment factor for each of said six joints based upon the three-dimensional image; and
  relatively rotating or translating each said pair of adjacent parts of said six joints about its respective axis in view of its respective adjustment factor for executing said fraction reduction.

According to a further aspect of the present invention, a fracture reduction system for reducing fracture of a fractured bone, the fractured bone having first and second portions about a fracture site, includes:
  a bone reposition device attachable to the fractured bone, the bone reposition device including
    first and second bone supports for supporting said first and second bone fragments;
    a plurality of sequentially connected connection members; and a plurality of joints each with at least a pair of adjacent parts for connecting the connection members therebetween and to the first and second bone supports, wherein the plurality of joints includes at least six joints, each of which possesses one degree of freedom and allows controllable relative rotation or translation of said pair of adjacent parts about its respective axis, and wherein the six axes extend at a degree relative to each other, a three-dimensional medical imaging device for scanning the fractured bone and the marker holders for obtaining a three-dimensional image of the fracture bone and the marker holders, and a computing device for determining an adjustment factor for each of said six joints based upon the three-dimensional image, wherein each said pair of adjacent parts of said six joints is relatively rotated or translated about its respective axis in view of its respective adjustment factor for executing said fraction reduction.

Other aspects and advantages of the invention will become apparent from the following detailed description, taken in conjunction with the accompanying drawings, which description illustrates by way of example the principles of the invention.

BRIEF DESCRIPTION OF THE DRAWINGS

FIG. 4 is a rear view of a rail member of the device of FIGS. 1 and 2;

FIG. 5 is a front view of a connection member of the device of FIGS. 1 and 2;

FIG. 6 is a side view of a fiducial marker holder of the device of FIGS. 1 and 2;

FIG. 7 is a side view of a pin offset locator of the device of FIGS. 1 and 2;

FIG. 8 is an explosive view of the pin offset locator of FIG. 7 and a bone pin;

DETAILED DESCRIPTION

One skilled in the art will recognize that the conventional external fixator designs may lack of controllable adjustability and the current external fixator applications lack of systematic methods to plan for how to apply and adjust an external fixator to facilitate bone reposition, which make the conventional applications difficult and subjective. Given that the deformity at the fracture site possesses six degrees of freedom (i.e., three translational and three rotational degrees of freedom about a set of three orthogonal axes), in order to accomplish the bone realignment process, an external fixation device may need at least six degrees of freedom.

Figure 1:
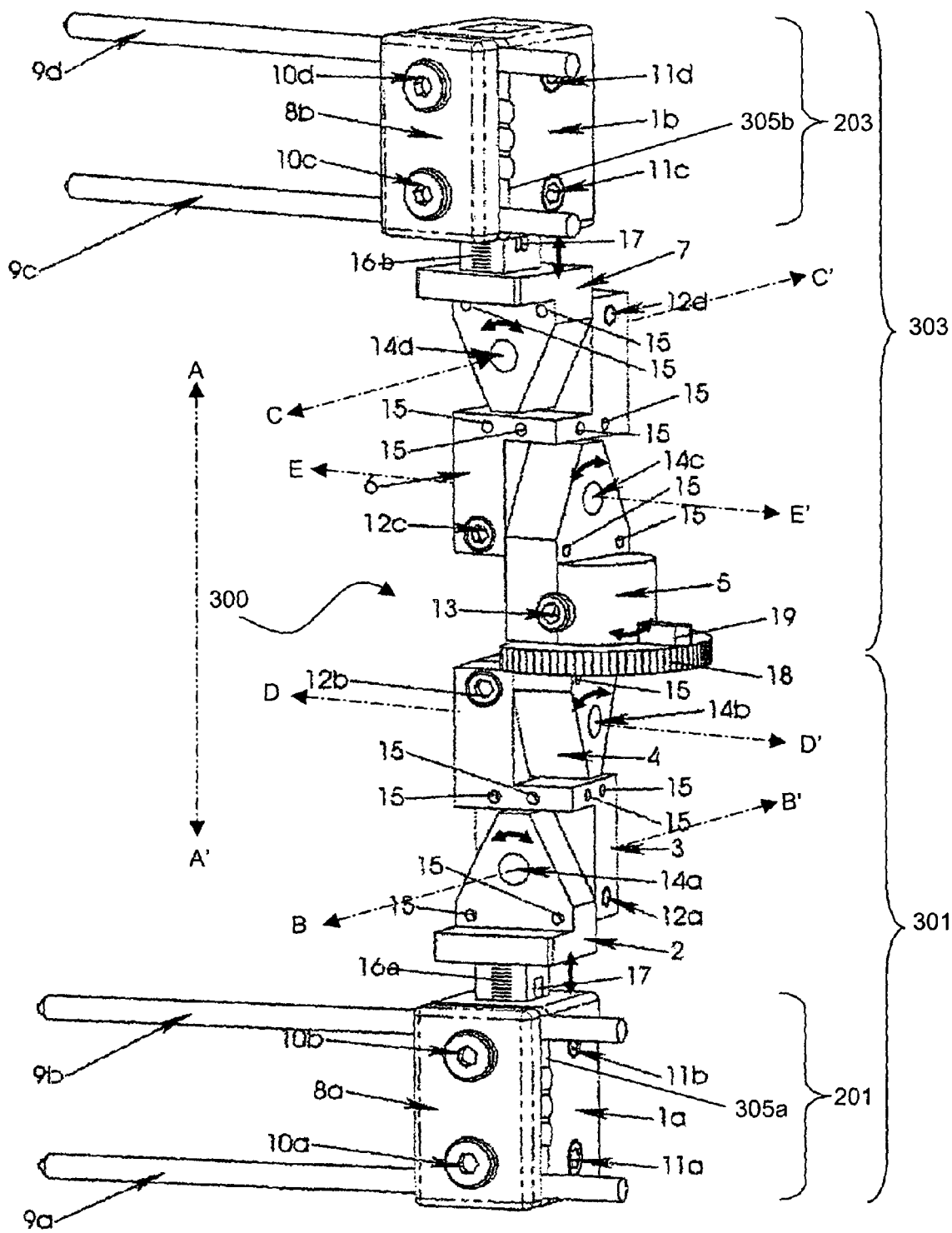
FIG. 1 is a perspective view of a bone reposition device according to an exemplary embodiment of the present invention, the bone reposition device being at its neutral configuration without transducers and corresponding mounting components.
Figure 2:
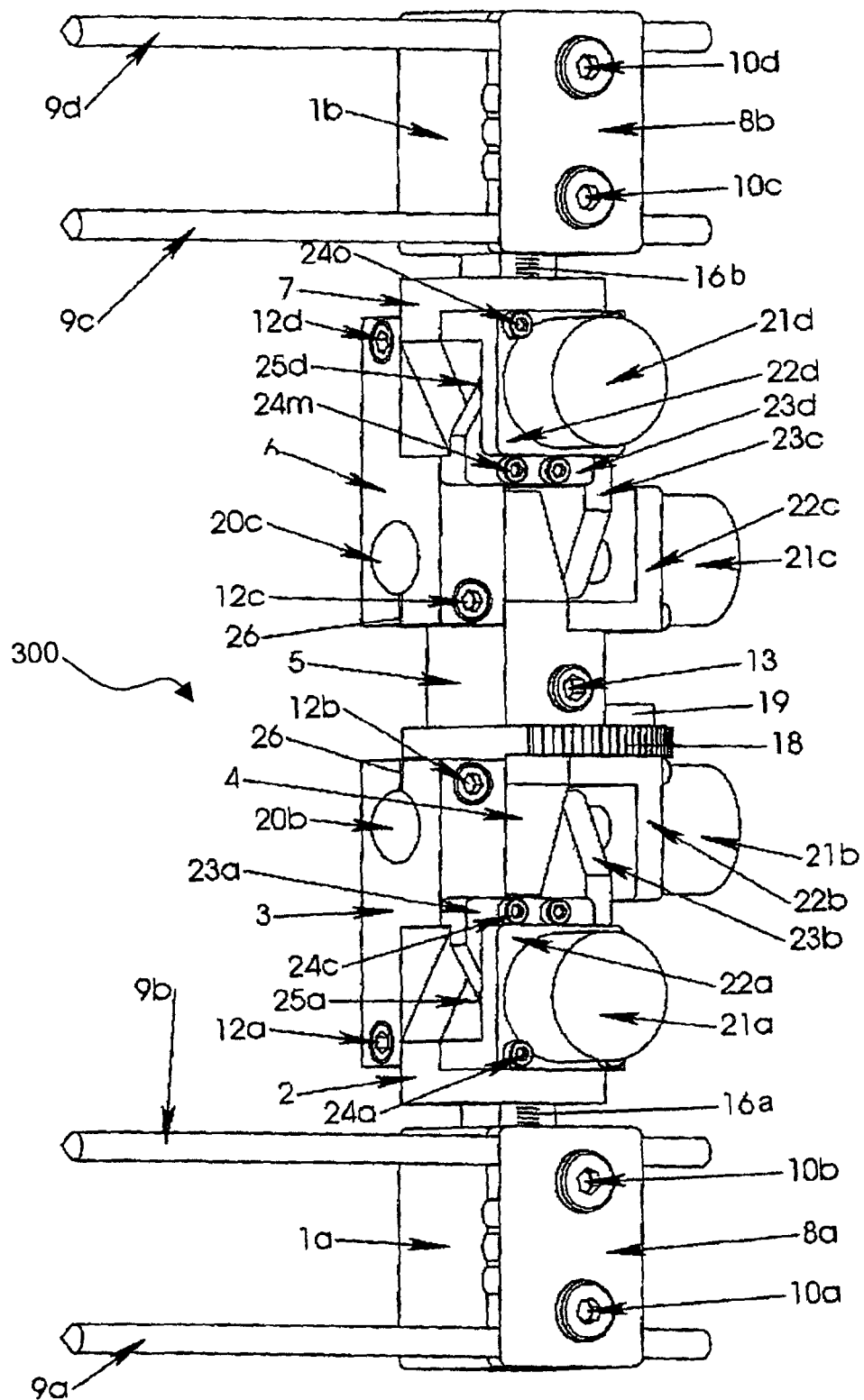
FIG. 2 is a perspective view of the device of FIG. 1, with the transducers and corresponding mounting components.

FIGS. 1 and 2 illustrate an exemplary bone reposition device 300 embodiment according to the present invention at its neutral configuration. The bone reposition device 300 includes a proximal and a distal portion 301, 303 connected through a central rotary joint 42 (see FIG. 9) and rotatable relative to each other about axis A-A'. Each of the distal and proximal portions includes pin clamp assembly 201, 203, rail member 2, 7, connection member 3, 6, and rotary join member 4, 5, connected in series and extending longitudinally along axis A-A' at its neutral configuration. Pin assemblies 1a, 1b and rail members 2, 7 are respectively connected through measurement scales 16a, 16b, which allow relative linear movements therebetween along axis A-A'. Rail members 2, 7 and connection members 3, 6 are respectively connected through shafts 14a, 14d, which function as a hinge joint and allow rotation relative to each other about axes B-B' and C-C' respectively. Connection members 3, 6 and rotary joint members 4, 5 are respectively connected through shafts 14b, 14c, which function as a hinge joint and allow rotation relative to each other about axes D-D' and E-E' respectively. In the exemplary embodiment, at the neutral configuration of the device 300, axes A-A', B-B' and D-D' are at least substantially perpendicular to each other; axes, C-C' and B-B' are at least substantially parallel to each other; axes, D-D' and E-E' are at least substantially parallel to each other. A person skilled in the field would appreciate that different orientations of these axes may also be suitable.

Thus, the bone reposition device 300 basically includes 7 joints 16a, 14a, 14b, 42, 14c, 14d, 16b connecting various parts; each joint has two adjacent parts and posses one degree of freedom. As described as follows, each join can facilitate continuous and controllable adjustments.

Figure 12:
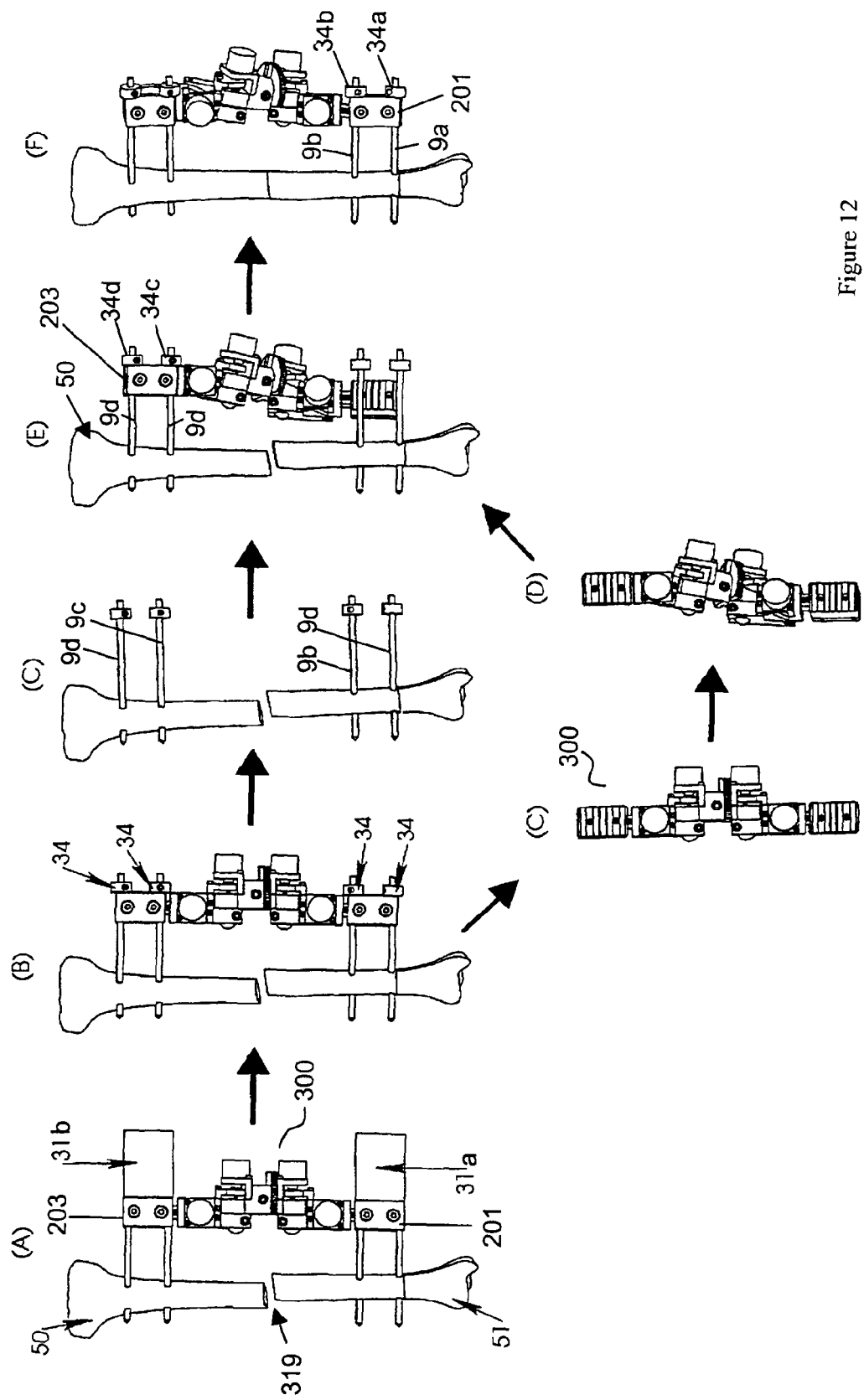
FIGS. 12a-f and c' illustrate the work flow of an exemplary fracture reduction process according to another aspect of the present invention.

Each pin clamp assembly 201, 203 includes a pin clamp body 1a, 1b; a pin blanket 8a, 8b; and a pair of bone pins 9a, 9b, 9c, 9d for inserting into respective bone fragments 51, 50 (see FIG. 12a). The bone pins can thus have their positions, and hence the bone fragments 51, 50, controlled by the bone reposition device 300. Grooves are provided on a side surface 305a, 305 b of each pin clamp body 1a, 1b. The bones pins 9a-9d are clamped between the respective side surfaces 305a, 305b and two pin blankets 8a, 8b by using screws 10a-d extending through the pin blankets 8a, 8b into the pin clamp bodies 1a, 1b. In this way, by loosening the screws 10a-d, the bone reposition device 300 can be detached from the bone pins 9a-d. Both ends of the bone pins 9a-d extend outside the respective pin clamp assemblies, one end to penetrate into bone fragments, the other end to allow attachment of accessories, which will be discussed in details with reference to FIGS. 6-8.

Set screws 11a-d, extending into the interior of the pin clamp bodies, function to tighten the pin clamp bodies 1a,1b on the respective grooves 17a,17b of the rail members 2,7 such that they are fixedly connected.

Transducers 21a-d are attachable to respective rail members 2, 7 and rotary joint members 4, 5 through first and second mounting members 22a-d, 23a-d and screws 24a-p for ascertaining relative rotation between respective rail member-connection member and connection member-rotary joint member pairs. The transducers are also connected to a computer (not shown) for measurement purpose. The measurement scales 16a, 16b, 18 and transducers 21a-d thereby provide the bone reposition device with accurate adjustment capabilities.

Figure 3:
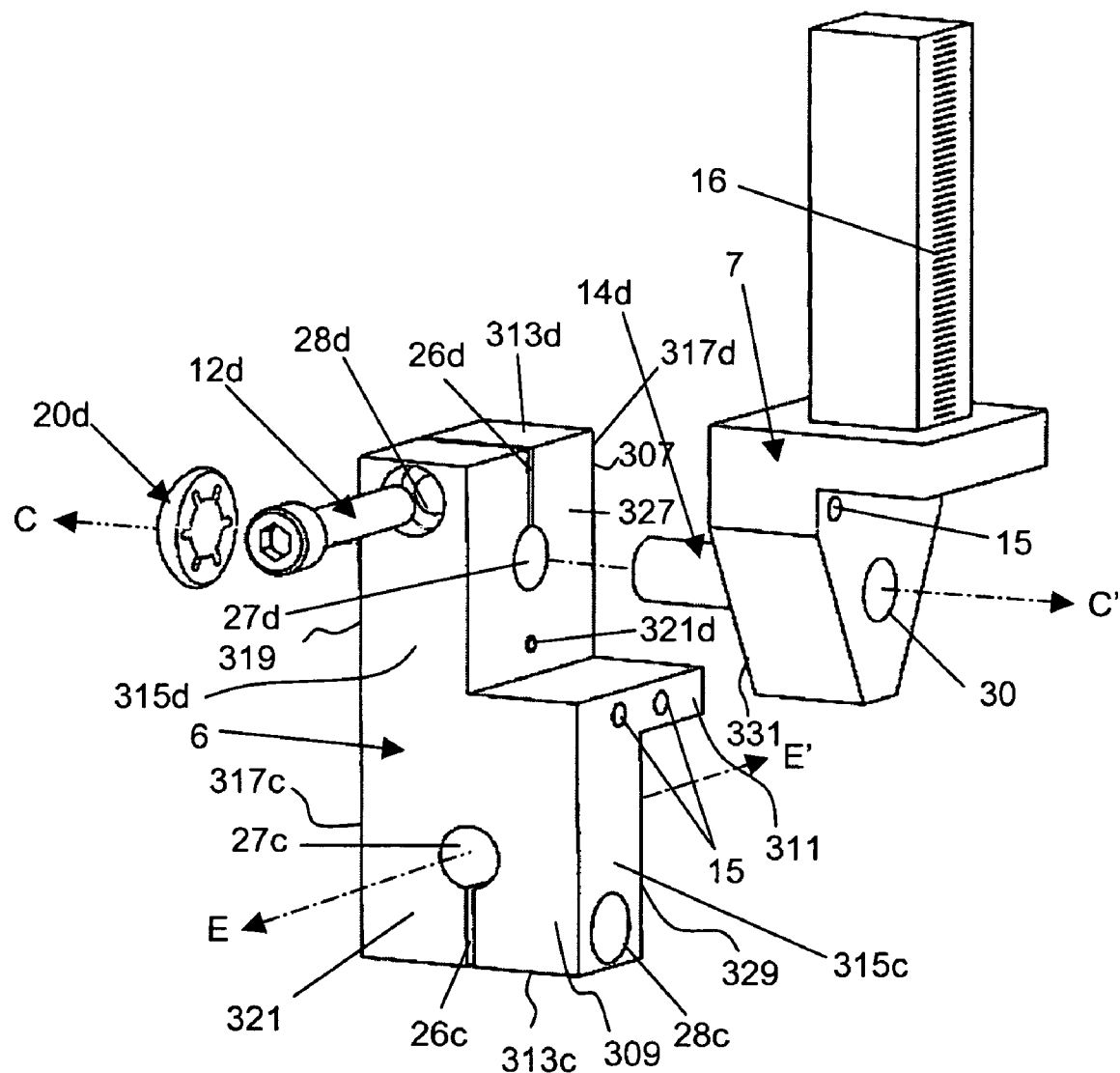
FIG. 3 is an explosive view of a hinge joint of the device of FIGS. 1 and 2.

FIGS. 3, 4, 5 illustrate the connection between the connection member and adjacent parts, using connection member 6 as an example. The connection member 6 has a pair of walls 307, 309 at least substantially perpendicular to each other and connected through a platform 311. Each wall has a circular shaft hole 27d, 27c for receiving shafts 14d, 14c of the rail member 7 and rotary joint member 5 (not shown in FIG. 3) respectively. The shaft 14d, 14c is press-fitted to shaft hole 30, 40 of the rail member 7 and rotary joint member 5 respectively at one end. At the other end, it extends outside the back surface 319, 321 of the wall 307, 309 to allow attachment of a button 20d, 20c for constraining the translation of the rail member 7 and rotary joint member 5 with respect to the connection member 6 along the shafts 14d, 14c respectively. Two slots 26d, 26c, each extending from the respective shaft holes 27d, 27c to an upper and a bottom surface 313d, 313c of the connection member 6, are created on the walls 307, 309 respectively. Such slots provide the walls of the connection member a certain amount of resilience. Two non-thread holes with counterbores 28d, 28c are created, extending from two side surfaces 315d, 315c of the walls 307, 309 until the slots 26d, 26c respectively. Two thread holes 29, which are concentric with the non-thread holes 28d, 28c, are created, extending from the slots 26d, 26c until the two side surfaces 317d, 317c respectively. Through the shaft 14d, shaft hole 27d, slot 26d, screw 12d, non-thread hole 28d, thread hole 29, and button 20d, continuous relative rotation between rail member 7 and connection member 6 can be achieved with the joint stiffness being controlled. It can be understood that connections between the various connection members and rail members or rotary joint members can be achieved similarly.

Two ball-nose spring plungers 321d, 321c are inserted at the front surfaces 327, 329 of the walls 307, 309 of the connection member 6, when mate with two holes located at the back surfaces 331, 333 (see FIG. 9) of the rail member 7 and the rotary joint member 5 respectively, allow positioning of the hinge joints at their neutral position.

FIG. 6 illustrates a fiducial marker holder 31 attachable to the other end of the bone pins 9a-d. Holes 32 are provided on the marker holder 31 for the bone pins to pass through. Three chrome coated stainless steel fiducial markers of 1 mm in diameter are embedded on its outermost surface and are not aligned in one single line as shown in FIG. 6 so as to be used to define local coordinate systems of the fractured bone fragments. In the exemplary embodiments, two fiducial marker holders are provided for being attached to the two pin assemblies respectively.

Figure 13:
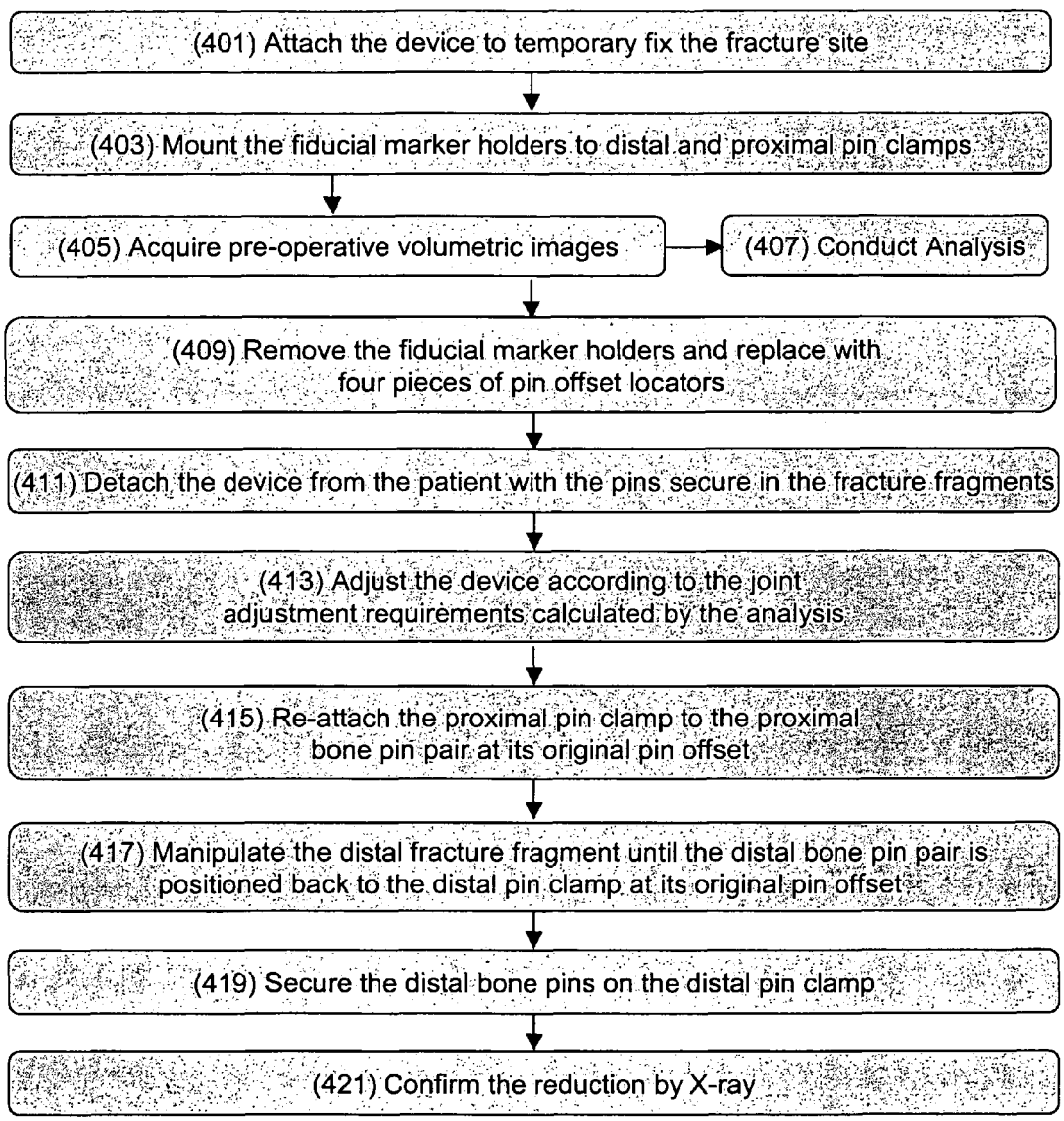
FIG. 13 illustrates the operation work flow of the process of FIG. 12.

FIGS. 7 and 8 illustrate a pin offset locater 34 attachable to a bone pin generally indicated by reference number 9. The pin offset locater 34 is generally circular in shape, and has a hole 36 for allowing the bone pin 9 to pass through and a threaded hole 35 for tightening the pin offset locater 34 on the bone pin 9 through a set screw 37. In the exemplary embodiments, four pin offset locaters are provided for the four bone pins 9a-d respectively for repositioning the proximal pin clamp assembly 203 of the bone reposition device 300 and guiding the manipulation of the distal fracture fragment 51 during the adjustment process, which will be discussed in details with reference to FIGS. 12, 13

Figure 9:
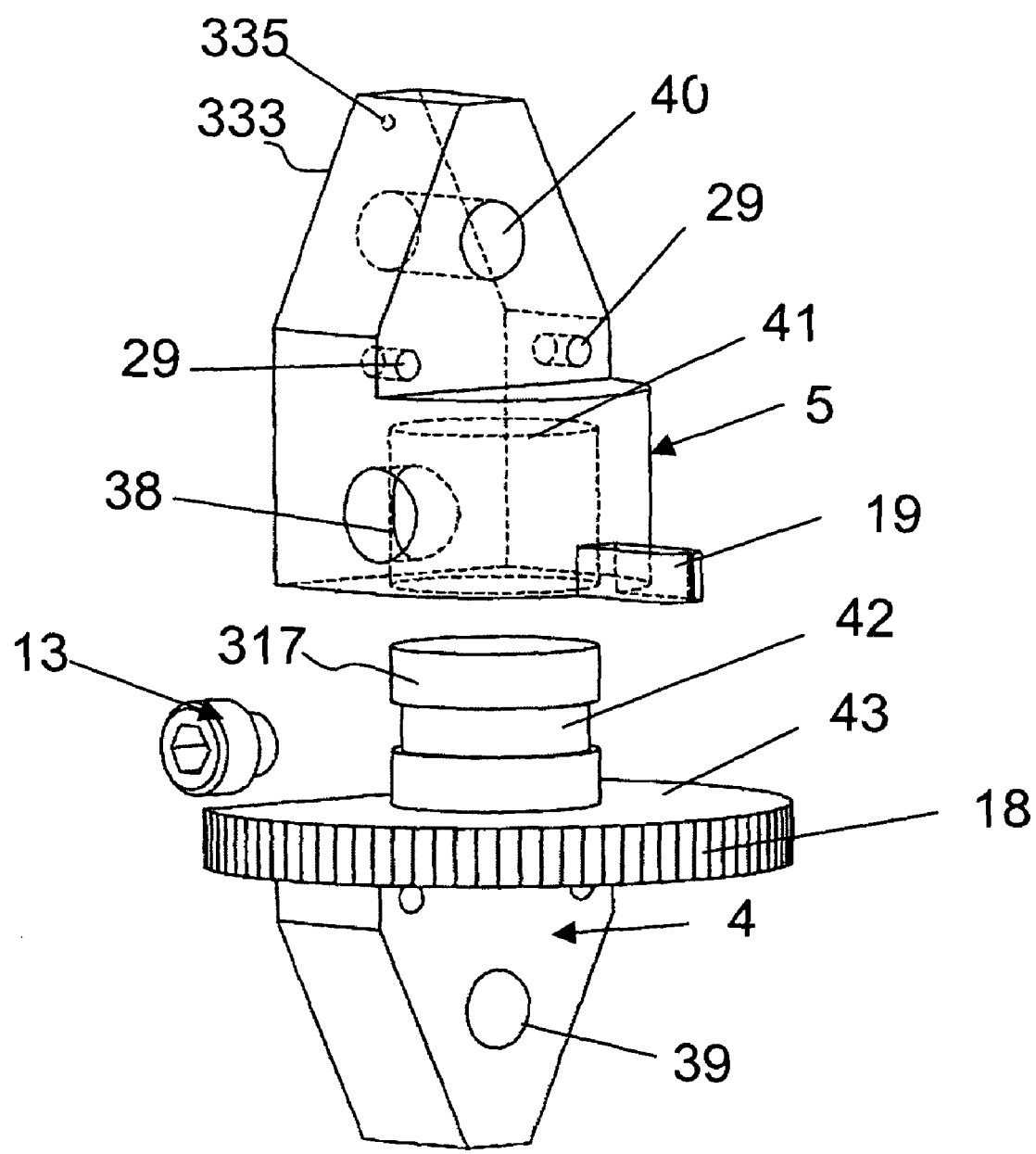
FIG. 9 is an explosive view of a central rotary joint of the device of FIGS. 1 and 2.

FIG. 9 illustrates the connection between the rotary joint members 4, 5. As shown in FIG. 8, the measurement scale 18 is mounted atop rotary joint member 4. A column 317 extending upwards from the measurement scale 18 is received in a cylindrical cavity 41 created in the rotary joint member 5. The column 317 has a circular groove 42 for engaging a set screw 13 penetrating from exterior into the cavity 41 through a thread hole 38 created on a side wall of the rotary joint member 5. In this way, continuous relative rotation between the two rotary joint members can be achieved with joint stiffness being controllable.

Figure 10:
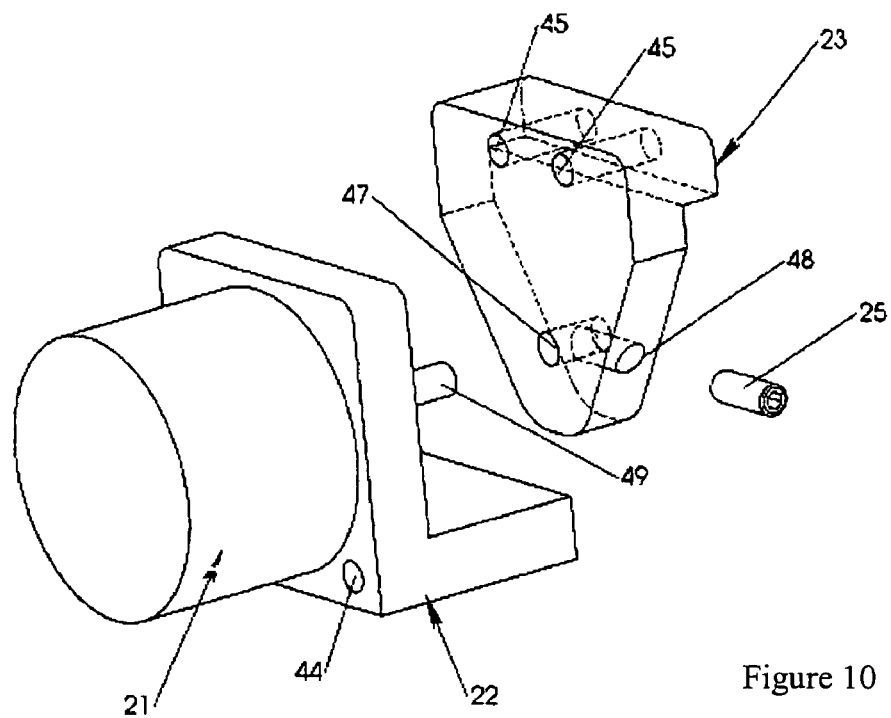
FIG. 10 is an explosive view of a transducer mounting set of the device of FIG. 2.
Figure 11:
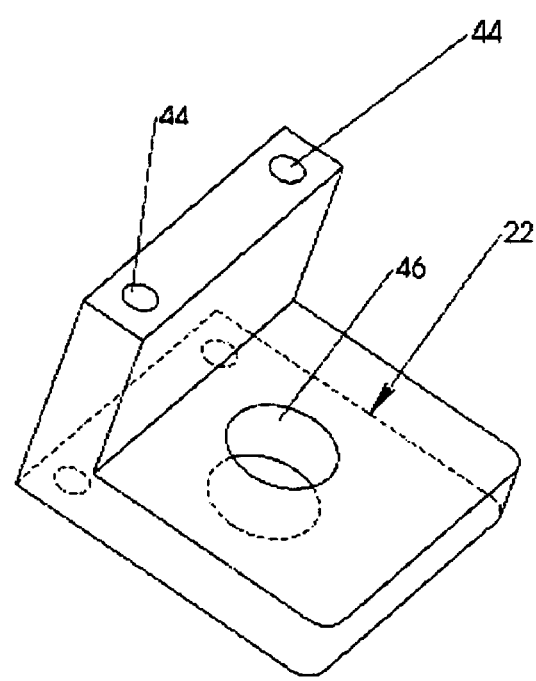
FIG. 11 is a perspective view of a first mounting member of the device of FIGS. 1 and 2.

FIGS. 10 and 11 illustrate the structure of one of the detachable transducers generally indicated by reference number 21. The transducer 21 is attached onto its respective rail member or rotary member through a first mounting member 22 that is basically a planar platform, a transducer mounting shaft 49 extending from the first mounting member and being inserted into a receptacle hole 47 on a second mounting member 23 that is basically another planar platform. The second mounting member 23 is attached on its respective connection member. Such an assembly can be fixed and mounted to the bone reposition device 300 through various screws 24 (see FIG. 2), thread holes 15, and holes 44, 45.

Process for fracture reduction are described as follows with reference to FIGS. 1, 2, 12a-f, 12c' and 13-15 as an exemplary application of the bone reposition system.

In step 401, the bone reposition device 300 is attached to the bone fragments 50, 51 of a patient (not shown) in any known initial configuration to temporarily fix the fracture site 319, which defines the initial deformity. In step 403, the fiducial marker holders 31a, 31b are attached to the pin clamp assemblies 201, 203 as shown in FIG. 11a. In step 405, pre-operative volumetric images are obtained by using computed tomography (CT) or ISO-C3D three-dimensional medical imaging technologies to scan along the fracture fragments 50, 51. In step 407, the CT or ISO-C3D slices are analyzed by a computer (not shown) to determine joint adjustment factors for fracture reduction. These factors determine the adjustment scales for each joint of the bone reposition device 300. Such analysis will be described in further details below with reference to FIGS. 13 and 14.

In step 409, the fiducial marker holders are removed, and the four pieces of pin offset locators 34 are mounted to the bone pins 9 of the pin assemblies and are in close contact with a side surface of the pin assemblies, as shown in FIG. 12b.

In step 411, the bone reposition device 300 is detached from the patient with the bone pins 9 secured in the bone fragments 50, 51 and the pin offset locators 34 secured on the bone pins 9, as shown in FIGS. 12c and 12c'. This can be achieved by loosening the screws 10a-d on the pin clamp blankets 8a, 8b.

In step 413, as shown in FIG. 12d, the bone reposition device 300 is adjusted in accordance with the join adjustments factors calculated during the analysis step 407. Specifically, the pin clamp assemblies 201, 203 are moved along the measurement scales 16a, 16b relative to the rail members 2, 7; the rail members 2, 7, connection members 3, 6 and rotary joint members 4, 5 are rotated relative to each other about their respective joints or shaft 14a-d and 317. The measurement scales 16a, 16b, 18 and the transducers 21a-d provide accurately measure of the adjustments. The various screws 11a-d, 12a-d, 13 on the bone reposition device 300 are tightened afterwards to secure the adjustments.

In step 415, the proximal pin clamp assembly 203 is re-attached and secured to the proximal bone pins 9c, 9d with the side surface aligned with the respective pin offset locators 34c, 34d, as shown in FIG. 12e.

In step 417, the distal bone fragment 51 is manipulated by a surgeon until the distal bone pins 9a, 9b are positioned back to the distal pin clamp assembly 201 at the original pin offset distance defined by the respective pin offset locators 34a, 34b. In other words, the side surface of the distal pin clamp assembly 201 is aligned with the respective pin offset locators 34a, 34b as shown in FIG. 12f. It can be understood that the distal bone fragment 51 is adjusted to its desired position during step 417 since the bone reposition device has been adjusted as desired, since all the joints on the bone reposition devise have been tightened, and since the proximal pin clamp assembly 203 is re-positioned in align with the respective pin offset locators 34c, 34d.

After the manipulation, in step 419, the distal bone pins are secured on the distal pin clamp assembly 201.

In step 421, the fracture reduction can be confirmed by scanning through an X-ray device, and the fracture reduction process is then completed.

It can be understood that the bone reposition system for performing the above-mentioned process would have firstly the above described bone reposition device, a three-dimensional medical imaging device for scanning the fractured bone along the fracture fragments for obtaining a three-dimensional image of the fracture fragments, and a computing device for determining an adjustment factor for each of said seven joints based upon the three-dimensional image, though such three-dimensional medical imaging device and computing device are not shown in the figures.

Figure 14:
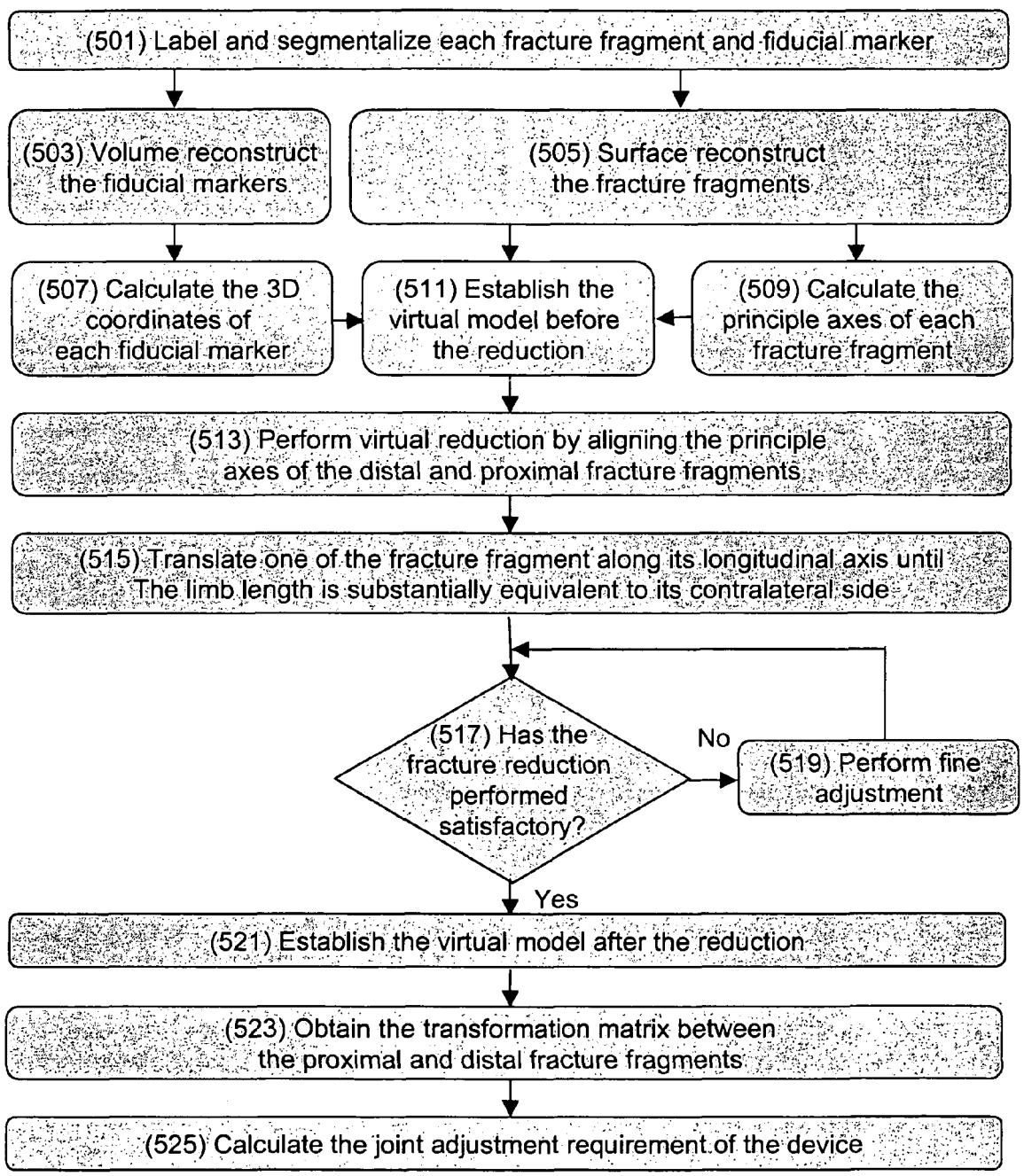
FIG. 14 illustrates the analysis work flow of part of the process of FIG. 13.
Figure 15:
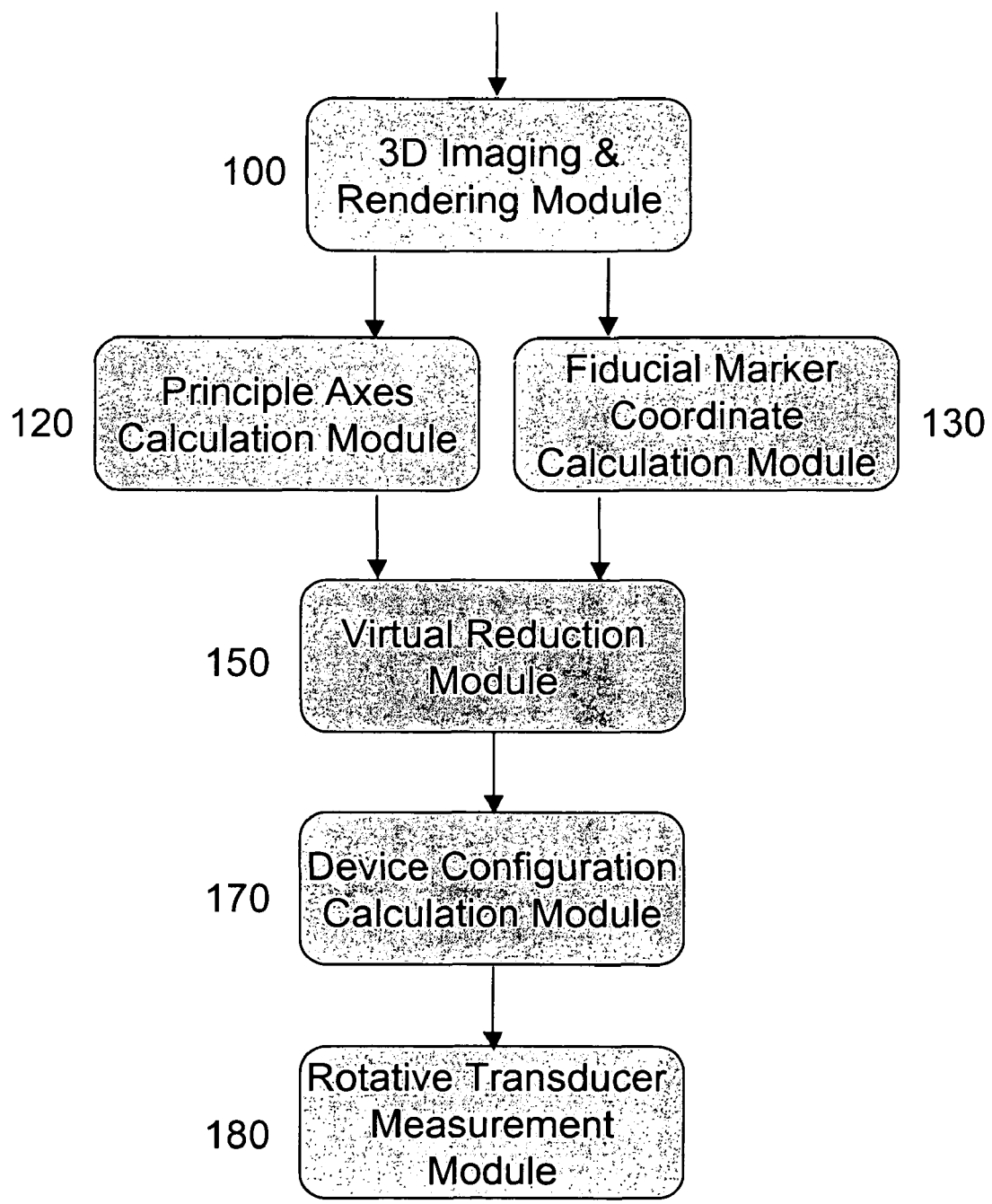
FIG. 15 illustrates the software architecture of the bone reposition system.

Referring to FIGS. 14 and 15, in steps 501 and 505, the CT or ISO-C3D slices are segmentalized, labeled and reconstructed to form the surface models of the distal and proximal bone fragments by using the 3D imaging and rendering module 100 as generally understood in the art.

In step 507, three-dimensional coordinates of centers of the chrome coated stainless steel fiducial markers are calculated from the volumetric data of the fiducial markers reconstructed in step 503 by a fiducial marker coordinate calculation module 130 using an automated center-of-gravity calculation algorithm. Such algorithm is generally known to the person skilled in the art and is disclosed in, for example, Ellis, R., et al., 1996, "Use of a Biocompatible Fiducial Marker in Evaluating the Accuracy of CT Image Registration," Investigative Radiology 31, 658-667, which is herein incorporated by reference. Since the proximal (distal) fracture fragment 50, 51 the proximal (distal) bone pins 9c,d, 9a,b; the proximal (distal) pin clamp assembly 203, 201; and the proximal (distal) fiducial marker holder 31b, 31a are rigidly linked together, the 3D coordinates of the fiducial markers can then be used to define the local coordinate systems for the proximal and distal bone fragments.

In step 509, principle axes of each bone fragment can be identified from the surface data of each bone fragment reconstructed in step 505 by a principle axes calculation module 120 using the principle axis transformation technique. Such technique is generally known in the art and has been disclosed in, for example, Tsao, J., et al., 1998, "Computer-assisted Quantification of Periaxial Bone Rotation from X-ray CT," Journal of Computer Assisted Tomography 22, 615-620, which is herein incorporated by reference.

In step 511, the surface models, 3D coordinates of the fiducial markers, and the principle axes of the proximal and distal bone fragments that represent their spatial positions and orientations prior to fracture reduction, are imported into a virtual reduction module 150, which is basically a native VRML authoring software in the exemplary embodiment, to establish a virtual model for manipulation.

In the manipulation of the virtual model, firstly, in step 513, the principle axes of the distal and proximal bone fragments are aligned with each other. This reduces the fracture deformity from a six degrees-of-freedom to a one degree-of-freedom issue, i.e., along the longitudinal axes. In step 515, the axial displacement is reduced by translating one of the bone fragments along its longitudinal axis until the limb length is substantially equivalent to that of the contralateral side.

In steps 517 and 519, fine tuning of the virtual model can be performed, and in step 521, a finalized virtual model can be established after the "virtual" fracture reduction by using the computer.

After the "virtual" reduction, in step 523, the 3D coordinates of the fiducial markers are used to estimate the desired transformation matrix between the proximal and distal bone fragments. Then in step 525, the desired transformation matrix is used by a device configuration calculation module 170 to calculate the joint adjustment factors for fracture reduction. Such calculation can be generally understood in the art and has been disclosed in, for example, Kim Y. H. et al., 2002, "Kinematic Simulation of Fracture Reduction and Bone Deformity Correction Under Unilateral External Fixation," Journal of Biomechanics 35 (2002) 1047-1058, which is herein incorporated by reference.

The foregoing discussion discloses and describes merely exemplary embodiments of the present invention applied to fracture reduction. Various alternatives can be made to the above described embodiment. For example, instead of manual adjustments, motors such as step motors can be connected to the various rotary and translational joints for driving and controlling the adjustments.

Furthermore, as could be understood in the art, a bone reposition device with six joints, each of which possesses one degree of freedom, would result in an unique joint adjustment factor for each joint that reduces a given fracture deformity. However, as could be understood in the art, a bone reposition device with more than six joints, each of which possesses one degree of freedom, would result in multiple joint adjustment schemes that could reduce a given fracture deformity. A skilled person in the field would also appreciate that each of the six joints can be rotational or translational.

In addition, apart from fracture reduction, various applications that require positioning two bone segments relative to each other can also be accomplished using the above described embodiment or its alternatives. Limb lengthening and osteotomy are some of the examples.

What is claimed is:

1. A bone reposition device, comprising:
first and second bone supports for supporting first and second portions of a fractured or osteotomized bone about a fracture or osteotomize site;
first and second marker holders attachable to the first and second bone supports;
the first and second marker holders respectively include first and second fiducial markers for defining relative orientations and positions of the first and second bone portions, respectively, and
each fiducial marker having a fixed position relative to its respective bone portion when the marker holders are attached to the bone supports, respectively,
a series of connection members extending between the first and second bone supports; and
a plurality of joints each having a single degree of freedom of movement and providing relative movement between adjacent connection members and between connection members adjacent the first and second bone supports,
the plurality of joints including at least six joints and allowing controllable relative rotation or translation of the first bone support relative to the second bone support about six degrees of freedom, the first and second fiducial markers for determination of an adjustment factor being representative of a relative displacement required to move the first and second bone portions to a reduced arrangement;

the first and second bone supports being disengageable from the bone portions so as to allow the joints to be moved and locked relative to each other and in accordance with the adjustment factor, and the first and second bone supports being reattachable to the respective bone portions after the joints are moved and locked relative to each other in accordance with the adjustment factor so as to maintain the first and second bone portions at said reduced arrangement.

2. The bone reposition device of claim 1, wherein the six joints are about one of a set of three joints, at its neutral configuration, and the three joints are at least substantially perpendicular to each other.

3. The bone reposition device of claim 1, wherein the first and second bone supports each includes at least two elongate members for attaching to the respective bone portion.

4. The bone reposition device of claim 3, further comprising first and second offset locaters attachable to the first bone support and third and fourth offset locaters attachable to the second bone support for reattaching the first and second bone supports to the elongate members after adjustment of the joints.

5. The bone reposition device of claim 4, wherein each offset locater is attachable to the respective elongate member.

6. The bone reposition device of claim 3, wherein each marker holder includes at least three non-collinear metal fiducial markers embedded on its external surface for defining a local coordinate system of its respective bone portion.

7. The bone reposition device of claim 1, further comprising at least six precision scales or position transducers attachable to the six joints respectively for controlling relative rotations of respective pair of adjacent parts.

8. The bone reposition device of claim 1, further comprising at least six motors, each being connected to one of the six joints or one of said pair of adjacent parts of one of said six joints respectively for driving relative rotation of said pair of adjacent parts.

9. The bone reposition device of claim 8, wherein said motors are designed to be stepping motors.

10. The bone reposition device of claim 1, wherein at least three of the said six joints each includes a projection extending outward from one of said pair of adjacent parts and fitting into a receptacle groove on the other adjacent part, and wherein size of said receptacle groove is adjustable such that stiffness of said three joints can be adjusted.

11. The bone reposition device of claim 1, wherein the first and second portions are rotatable relative to each other along a longitudinal axis, each of the first and second portions including two revolute joints and one telescopic joint, each of the joint possessing one degree of freedom and allowing relative rotation and translation respectively of said pair of adjacent parts about its respective axis respectively, and each of three axes being at a degree to each other and to the longitudinal axis.

12. The bone reposition device of claim 11, further comprising
four transducers attachable to said four revolute joints for measuring the adjustments thereof,
a measurement scale attachable to a joint about which the first and second portions rotates for measuring the adjustment, and
two measurement scales attachable to said two telescopic joints for measuring the adjustments.

13. A process for reducing fracture of a fractured bone, the fractured bone having first and second portions about a fracture site, said process comprising
attaching a bone reposition device to the fractured bone, the bone reposition device including
first and second bone supports for supporting said first and second bone portions;
first and second marker holders attachable to the first and second bone supports,
the first and second marker holders respectively include first and second markers for defining relative orientations and positions of the first and second bone portions respectively, wherein each marker has a fixed position relative to its respective bone portion when the marker holders are attached to the bone supports respectively,
a series of connection members extending between the first and second bone supports; and
a plurality of joints each having a single degree of freedom of movement and providing relative movement between adjacent the connection members and between connection members adjacent the first and second bone supports,
the plurality of joints including at least six joints and allows controllable relative rotation or translation of the first bone support relative to the second bone support about six degrees of freedom,
scanning the fractured bone for obtaining a three-dimensional image of the fracture fragments;
determining an adjustment factor representative of relative displacement required to move the first and second bone portions to a reduced arrangement by the first and second markers based upon the three-dimensional image; and
disengaging the first and second bone supports from the bone portions so as to allow the joints to be moved and locked relative to each other and in accordance with the adjustment factor, and
reattaching the first and second bone supports to the respective bone portions after the joints are moved and locked relative to each other in accordance with the adjustment factor so as to maintain the first and second bone portions at said reduced arrangement.

14. The process of claim 13, further comprising
scanning the fractured bone and the marker holders for obtaining a three-dimensional image of the fracture fragments and the marker holders.

15. The process of claim 14, further comprising
creating a virtual model of the fracture fragments using the three-dimensional image of the fracture fragments; and
reducing the fracture deformity within the virtual model.

16. The process of claim 15, further comprising
determining a desired transformation matrix between the first and second bone portions at the state "after reduction" using marker coordinates obtained from the three-dimensional image; and
determining an adjustment factor for each of said six joints based upon the said transformation matrix.

17. The process of claim 13, wherein the first and second bone supports each includes at least two elongate members detachably mounted to its respective bone support for attaching to the respective bone portion.

18. The process of claim 17, further comprising
attaching the first and second marker holders to the respective elongate members, wherein each marker holder includes at least three non-collinear markers for assisting to define relative orientations and positions of the first and second bone portions.

19. The process of claim 18, comprising
establishing local coordinate systems for the first and second bone portions with assistance of the markers; and
determining the adjustment factors in view of the local coordinate systems.

20. The process of claim 13, wherein the bone reposition device includes at least six precision scales or position transducers attachable to the six joints respectively for controlling relative rotations of respective pair of adjacent parts.

21. The process of claim 13, wherein the bone reposition device includes at least six motors, each being connected to one of the six joints or one of said pair of adjacent parts of one of said six joints respectively for driving relative rotation of said pair of adjacent parts.

22. The process of claim 13, wherein the scanning step is executed by using a three-dimensional medical imaging process.

23. The process of claim 22, wherein the scanning step is executed by using computed tomography technology.

24. The process of claim 13, wherein the first and second portions rotatable relative to each other along a longitudinal axis, each of the first and second portions including two revolute joints and one telescopic joint, each of the joint possessing one degree of freedom and allowing relative rotation and translation respectively of said pair of adjacent parts about its respective axis respectively, and each of three axes being at a degree to each other and to the longitudinal axis.

25. The process of claim 24, wherein the six axes are about one of the three axes at its neutral configuration, and wherein the three axes are at least substantially perpendicular to each other.

26. The process of claim 13, further comprising
ascertaining the principle axes of the first and second bone portions are at least substantially align;
ascertaining the limb length is at least substantially equivalent to that of the contralateral side; and
determining the adjustment factors in view of the principle axes and limb length.

27. A bone reposition system for reducing fracture of a fractured bone, the fractured bone having first and second portions about a fracture site, said system comprising:

a bone reposition device attachable to the fractured tone, the bone reposition device including
first and second bone supports for supporting said first and second bone fragments portions;
first and second marker holders attachable to the first and second bone supports, said first and second marker holders respectively include first and second markers for defining relative orientations and positions of the first and second bone portions respectively, and wherein each marker has a fixed position relative to its respective bone portion when the marker holders are attached to the bone supports respectively;
a series of connection members extending between the first and second bone supports; and
a plurality of joints each having a single degree of freedom and providing relative movement between adjacent connection members and between connection members adjacent the first and second bone supports,
the plurality of joints including at least six joints and allowing controllable relative rotation or translation of the first bone support relative to the second bone support about six degrees of freedom,
a three-dimensional medical imaging device for scanning the fractured bone and the marker holders for obtaining a three-dimensional image of the fractured bone and the marker holders, and
a computing device for determining an adjustment factor representative of a relative displacement required to move the first and second bone portions to a reduced arrangement based upon the three-dimensional image,
the first and second bone supports being disengageable from the bone portions so as to allow the joints to be moved and locked relative to each other and in accordance with the adjustment factor, and
the first and second bone supports being reattachable to the respective bone portions after the joints are moved and locked relative to each other in accordance with the adjustment factor so as to maintain the first and second bone portions at said reduced arrangement.

* * * * *